United States Patent
Regnier et al.

(10) Patent No.: US 11,357,994 B2
(45) Date of Patent: Jun. 14, 2022

(54) AUTONOMOUS CARDIAC IMPLANT OF THE LEADLESS CAPSULE TYPE, INCLUDING A PIEZOELECTRIC BEAM ENERGY HARVESTER

(71) Applicant: CAIRDAC, Antony (FR)

(72) Inventors: Willy Regnier, Longjumeau (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 42 days.

(21) Appl. No.: 17/133,825

(22) Filed: Dec. 24, 2020

(65) Prior Publication Data

US 2021/0316148 A1    Oct. 14, 2021

(30) Foreign Application Priority Data

Apr. 9, 2020  (EP) .................................. 20315142

(51) Int. Cl.
| | |
|---|---|
| *H02N 2/18* | (2006.01) |
| *A61N 1/378* | (2006.01) |
| *A61N 1/375* | (2006.01) |
| *H01L 41/113* | (2006.01) |
| *H02N 2/00* | (2006.01) |

(52) U.S. Cl.
CPC .......... *A61N 1/3785* (2013.01); *A61N 1/3756* (2013.01); *H01L 41/1136* (2013.01); *H02N 2/186* (2013.01); *H02N 2/22* (2013.01)

(58) Field of Classification Search
CPC ...... H02N 2/186; H02N 2/22; H01L 41/1136; A61N 1/3785; A61N 1/3756
See application file for complete search history.

(56) References Cited

U.S. PATENT DOCUMENTS

| | | | | |
|---|---|---|---|---|
| 9,095,716 | B2 * | 8/2015 | Makdissi | .............. A61N 1/3785 |
| 9,786,832 | B2 * | 10/2017 | Abdelkefi | ................ H02N 1/08 |
| 2007/0293904 | A1 * | 12/2007 | Gelbart | ................ A61N 1/3785 |
| | | | | 607/35 |
| 2009/0174289 | A1 * | 7/2009 | Tanner | ................ H01L 41/1136 |
| | | | | 310/339 |

(Continued)

FOREIGN PATENT DOCUMENTS

| | | |
|---|---|---|
| CN | 109980992 | 7/2019 |
| CN | 108540013 | 10/2019 |

(Continued)

*Primary Examiner* — J. San Martin
(74) *Attorney, Agent, or Firm* — CRGO Global; Steven M. Greenberg (57) ABSTRACT

An energy harvester includes a pendular unit subjected with a piezoelectric beam coupled to an inertial mass. On the clamped side of the beam, a beam frame includes two pressing elements between which the beam is taken in sandwich, each including i) an intermediate part, an internal face of which presses on a corresponding face of the beam, and ii) a pressure plate, an internal face of which presses on an external face of the intermediate part, a printed circuit board being interposed between them. The intermediate parts and the pressure plates are passed through by at least one common transverse bore receiving a locking pin. The intermediate parts, the pressure plates and the pin are each massive metal parts ensuring a direct electrical and mechanical contact with the electrodes of the beam and with the printed circuit boards.

16 Claims, 4 Drawing Sheets

(56) References Cited

U.S. PATENT DOCUMENTS

| | | | |
|---|---|---|---|
| 2016/0066849 A1* | 3/2016 | Baru | A61N 1/36557 |
| | | | 607/19 |
| 2017/0100597 A1* | 4/2017 | Barror | A61N 1/37223 |
| 2018/0185638 A1* | 7/2018 | Regnier | H02N 2/18 |
| 2019/0151666 A1* | 5/2019 | Bonnet | H02N 2/186 |
| 2019/0190404 A1 | 6/2019 | Karami et al. | |
| 2019/0381325 A1* | 12/2019 | Regnier | H02N 2/188 |
| 2020/0094048 A1* | 3/2020 | Regnier | A61N 1/37518 |
| 2020/0220067 A1 | 7/2020 | Rufer et al. | |
| 2020/0259427 A1* | 8/2020 | Nguyen-Dinh | A61N 1/3785 |

FOREIGN PATENT DOCUMENTS

| | | | |
|---|---|---|---|
| CN | 111817603 A * | 10/2020 | H02N 2/186 |
| CN | 113507235 A * | 10/2021 | |
| WO | WO-2006072539 A2 * | 7/2006 | B60C 23/041 |
| WO | WO-2007130634 A2 * | 11/2007 | A61B 1/00156 |

\* cited by examiner

Fig.10

AUTONOMOUS CARDIAC IMPLANT OF THE LEADLESS CAPSULE TYPE, INCLUDING A PIEZOELECTRIC BEAM ENERGY HARVESTER

CROSS REFERENCE TO RELATED APPLICATIONS

This application claims priority under 35 U.S.C. § 119(a) to European patent application number 20315142.8, filed on Apr. 9, 2020, the entire teachings of which are incorporated herein by reference.

BACKGROUND OF THE INVENTION

Field of the Invention

The invention relates to energy harvesting devices, also called harvesters or scavengers, which collect mechanical energy resulting from various movements they undergo and convert this mechanical energy into electrical energy, and more particularly to the harvesting devices of the so-called "PEH" (Piezoelectric Energy Harvester) type, which use as a mechanical-electrical transducer an oscillating piezoelectric beam coupled to an inertial mobile mass.

Description of the Related Art

In the field of medical implants, the recent advances in miniaturization of active devices and the advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system including a mechanical energy harvester associated with an integrated energy storage component, such as a rechargeable battery or a high-performance capacitor.

Indeed, one of the critical aspects of these miniaturized devices is the power autonomy. The life duration of such an implant being of about 8 10 years, taking into account the very small dimensions, it is not possible to use a conventional battery, even a high-density one.

The energy harvester addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, the vibrations of the cardiac tissues linked i.a. to closings and openings of the cardiac valves, or blood flow rate variations in the surrounding environment, which stress the implant and make it oscillate at the rhythm of the flow rate variations.

The mechanical energy collected by the harvester is converted into electrical energy (voltage or current), by means of a suitable mechanical electrical transducer, for powering the various circuits and sensors of the device and for charging the energy storage component. This power system allows the device to operate in full power autonomy during its whole life.

This energy harvesting technique is particularly well adapted for powering the implanted autonomous capsules having no physical connection with a remote device. Such capsules are called for this reason "leadless" capsules, for distinguishing them from the electrodes or sensors arranged at the distal end of a lead, through the whole length of which run one or several conductors connected to a generator connected to the opposite, proximal end.

The invention is nevertheless not limited to a particular type of capsule, nor even of implant, and it is applicable as well to many other types of devices, whatever the operational purpose thereof, cardiac or other, medical or not.

In the cardiac application case, the leadless capsule continuously monitors the rhythm of the patient and if necessary issues to the heart electrical pulses for stimulation, resynchronization and/or defibrillation in case of rhythm disorders detected by the capsule. The leadless capsule may be an epicardial capsule, fixed to the outer wall of the heart, or an endocavitary capsule, fixed to the inner wall of a ventricular or atrial cavity, or a capsule fixed to the wall of a vessel near the myocardium. The fixation of the capsule to the implantation site is made through a protruding anchoring system extending the capsule body and designed to penetrate the cardiac tissue, in particular by means of a screw.

The capsule further includes various electronic circuits, sensors, etc., as well as wireless communication transmission/reception means for the remote exchange of data, the whole being integrated in a body of very small size that can be implanted at sites whose access is difficult or that leave little space available, such as the apex of the ventricle, the inner wall of the atrium, etc.

WO 2019/001829 A1 (Cairdac) describes an example of such a leadless intracardial capsule.

There exist several types of energy harvesters, based on different physical principles: system of the automatic wind-up watch movement type, mobile magnet system, bellows system or similar system collecting the blood pressure variations, etc.

The invention more particularly relates to the capsules or similar implantable devices whose energy harvester uses an inertial pendular unit subjected to the above-described external stresses.

An inertial pendular unit implements a transducer including in the capsule a mobile mass, called "seismic mass" or "inertial mass", which is driven according to the movements of the capsule, permanently subjected to the various external stresses described hereinabove. After each of these stresses, the inertial mass, which is coupled to an elastically deformable element, oscillates at a natural frequency of free oscillation.

The mechanical energy of the oscillation is converted into electrical energy by a mechanical-electrical transducer producing an electrical signal. This signal is provided to a power management circuit of the capsule, which rectifies and regulates the electrical signal to output a stabilized direct voltage or current, for powering the various electronic circuits and sensors of the capsule, as well as for charging the energy storage component.

The mechanical-electrical transducer may be in particular a piezoelectric component cyclically and alternately stressed in bending so as to generate within its constituent material electrical charges that are collected at the surface of the component to be used by the self-powering system of the leadless capsule. This piezoelectric component may in particular be a piezoelectric beam clamped at one of its end and coupled to the inertial mass at its other end, which is free.

Such an energy harvester, of the PEH type, for powering an implant from the oscillations of a piezoelectric beam is described in particular in U.S. Pat. No. 3,456,134 A (Ko) and in above-mentioned WO 2019/001829 A1.

It will be noted that the term "beam" has to be understood in its widest meaning, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a width and/or a thickness that are not constant in the longitudinal direction, as well as, possibly, a deformability going beyond a single degree of freedom in bending.

Many technical difficulties have however to be solved to allow making PEHs that are, despite an extreme miniaturization, both extremely performing and perfectly reliable, with typically a life time without failure nor loss of efficiency of at least 10 years.

Experience shows in particular that one of these difficulties occurs critically at the clamping of the transducing beam, where the stress of the beam in its bending movement is maximum. Now, this is precisely this region, where the curvature of the bent beam is the highest, that generates the maximum of charges and hence the maximum of instantaneous electrical energy provided by the PEH.

The way the beam is clamped into the part that supports it and connects it to the capsule body is therefore a particularly tricky aspect of the design and making of a PEH, and consequently, of an efficient and reliable leadless implant.

In particular, it is important that the distribution of the pressure exerted on the material of the beam at the place where the latter is clamped is the most uniform possible, without thereby being:

neither too low, because it would be to the detriment i) of a good mechanical clamping making it possible to generate the desired bending stresses, and ii) of a good electrical contact with the surface electrodes of the beam (the electrical connection being possible only at the clamping, that is fixed);

not too high, as an excessive stress would be to the detriment of the reliability.

Moreover, the technical solutions involving bondings are to be avoided, because they are in the long term subject to oxidation and ageing phenomena, which hardly guarantee the absolute reliability required for this type of implanted devices.

Another important aspect which has to be taken into account is the accurate centring of the beam by the part that supports it, at the time of assembly of the different elements of the PEH.

WO 2018/122244 A1 (Regnier) describes in detail various arrangements trying to respond to these multiple constraints, such as:

squeezing the beam between two jaws subjected to radial forces controlled thanks to an elastically deformable ring, in particular an oval ring placed about these jaws;

overmoulding the clamped end of the beam previously to the mounting thereof, with possibly inclusion of rigid reinforcement elements; or gripping the beam between two jaws receiving a tightening effort exerted at the time of mounding by a clamp, then overmoulding a ring about these jaws in order to ensure the definitive holding of the beam after removal of the clamp effort.

However, these solutions are complex to industrialise as regards the mechanical manufacturing and the size tolerances of the different parts, hence expensive to implement. Moreover, the plastic material parts or the overmouldings remain very sensitive to ageing of the material in the very long term, hence they do not offer an absolute guarantee of the required reliability for a device implanted in the organism.

The object of the present invention is to solve all these difficulties, by proposing a PEH beam clamping structure that is simple to manufacture and to assemble, while guaranteeing a very high level of accuracy of the beam compression pressure, with an excellent reliability in the long term, by avoiding in particular the use of plastic material parts and/or bondings

BRIEF SUMMARY OF THE INVENTION

For that purpose, the invention proposes a medical device of the autonomous implantable capsule type, including, in a per se known manner from above-mentioned WO 2018/122244 A1, an energy harvesting module including an oscillating pendular unit subjected to external stresses applied to the device. The oscillating pendular unit includes an elastically deformable piezoelectric beam, with a clamped end and an opposite, free end coupled to an inertial mass, the piezoelectric beam being adapted to convert into an oscillating electrical signal the mechanical energy produced by the oscillations of the pendular unit. The tubular envelope of the device also houses a beam frame, the beam frame including two pressing elements between which the clamped end of the piezoelectric beam is taken in sandwich, and a means for tightening the pressing elements together.

Characteristically of the invention, each pressing element of the beam frame includes i) an intermediate part, an internal face of which presses on a corresponding face of the piezoelectric beam, and ii) a pressure plate, an internal face of which presses on an external face of the intermediate part. Moreover, the intermediate parts and the pressure plates of the two pressing elements are passed through by at least one common bore extending in a transverse direction with respect to a longitudinal axis of the piezoelectric beam, the at least one common bore receiving a locking pin. Finally, the beam frame includes a means for holding and fastening the pin in position into the at least one common bore.

According to various subsidiary advantageous features:

the means for holding and immobilizing the pin in position includes a laser welding of a free end of the pin at a open edge of the common bore;

the intermediate part, an internal face of which presses against a corresponding face of the piezoelectric beam is in mechanical contact with the corresponding face of the piezoelectric beam. Advantageously, this intermediate part further includes on its internal face a conductive material capable of further establishing an electrical contact with the corresponding face of the piezoelectric beam, at a surface electrode of the piezoelectric beam;

the device further includes a printed circuit board interposed between the intermediate part and the pressure plate of at least one of the pressing elements of the beam frame, and the pressure plate includes, on an internal face, a conductive material in electrical contact with the corresponding external face of the printed circuit board;

in the latter case, the intermediate part may include, on its internal face, a conductive material capable of establishing an electrical contact with the corresponding face of the piezoelectric beam, at a surface electrode of the piezoelectric beam, and includes, on its external face, a conductive material capable of establishing an electrical contact with an internal face of the printed circuit board, the conductive materials of the internal and external faces of the intermediate part being electrically coupled to each other. The intermediate part may in particular be a single-piece part formed of a single conductive material;

the intermediate parts, the pressure plates and the pin are each massive metal parts;

the beam frame is essentially devoid of element interposed between the intermediate parts and the clamped end of the piezoelectric beam, and/or essentially devoid of bonding points;

the elongated tubular envelope also houses a support part of external tubular shape conjugated to the internal shape of the tubular envelope, and including at one of its ends a receptacle capable of receiving and centring the beam frame and of fastening the latter by press-fit at external faces of the pressure plates; and/or the pin is a metal part coated with an electrically insulating material adapted to avoid a galvanic connection and/or a leak current within the piezoelectric beam.

The present invention also relates to a method for manufacturing a device as set forth above, the method including the following steps:

obtaining a piezoelectric beam;

placing two pressing elements on either side of a clamped end of the piezoelectric beam, each pressing element including i) an intermediate part, an internal face of which presses on a corresponding face of the piezoelectric beam, and ii) a pressure plate, an internal face of which presses on an external face of the intermediate part, with, as the case may be, a printed circuit board interposed between the intermediate part and the pressure plate of at least one of the pressing elements of the beam frame;

positioning a pin into a common bore passing through the intermediate parts and the pressure plates of the two pressing elements in a transverse direction with respect to a longitudinal axis of the piezoelectric beam;

pressing the beam under controlled pressure between the two pressing elements, until reaching a predetermined transverse force of clamping of the piezoelectric beam between the two pressing elements; and while maintaining the predetermined transverse force, definitively fastening the pin into the at least one common bore.

According to various advantageous implementations of the method:

step e) is a step of laser welding a free end of the pin to an open edge of the common bore;

the method is essentially devoid of bonding step; and/or the controlled pressure exerted on the beam between the two pressing elements is included between at least 0.1 MPa and at most 10 MPa.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

An exemplary embodiment of the device of the invention will now be described, in an application to an autonomous implantable capsule intended to be implanted into a cardiac cavity.

As indicated hereinabove, this particular application is not limitative of the invention, whose teachings may be applied to many other types of autonomous devices incorporating an energy harvester of the PEH type, whether these devices are implantable or not, medical or not.

Figure 1:
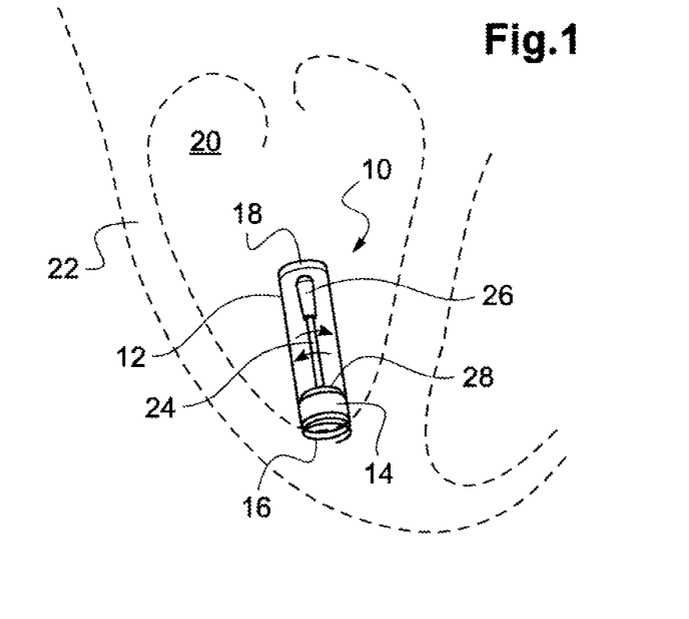
FIG. 1 illustrates a medical device of the leadless capsule type in its environment, implanted in the bottom of the right ventricle of a patient.

FIG. 1 shows a leadless capsule device 10 in a cardiac stimulation application.

The capsule 10 is made in the external form of an implant with an elongated cylindrical tubular envelope 12 enclosing the various electronic and power supply circuits of the capsule, as well as an energy harvester with a pendular unit. The typical dimensions of such a capsule are a diameter of the order of 6 mm for a length of about 25-40 mm.

The tubular envelope 12 has, at its front (distal) end 14, a protruding anchoring element, for example an helical screw 16, to hold the capsule on the implantation side. Other anchoring systems can be used, and do not modify in any way the implementation of the present invention. The opposite (proximal) end 18 of the capsule 10 is a free end, which is only provided with means (not shown) for the temporary connection to a guide-catheter or another implantation accessory used for the implantation or explantation of the capsule, which is then detached from the latter.

In the example illustrated in FIG. 1, the leadless capsule 10 is an endocavitary implant implanted into a cavity 20 of the myocardium 22, for example at the apex of the right ventricle. As a variant, still in a cardiac stimulation application, the capsule may also be implanted on the interventricular septum or on an atrial wall, or also be an epicardial capsule placed on an external region of the myocardium, wherein these different implantation modes do not modify in any way the implementation of the present invention. To perform detection/stimulation functions, an electrode (not shown) in contact with the cardiac tissue at the implantation site collects cardiac depolarization potentials and/or applies stimulation pulses. In certain embodiments, the function of this electrode may be provided by the anchoring screw 16, which is then an active screw, electrically conductive and connected to the detection/stimulation circuit of the capsule.

The leadless capsule 10 is moreover provided with an energy harvesting module, called "PEH", including an inertial pendular unit that oscillates, inside the capsule, following the various external stresses to which the capsule is subjected. These stresses may in particular result from: the movements of the wall to which the capsule is anchored, which are transmitted to the tubular body 12 by the anchoring screw 16; and/or the blood flow rate variations in the medium surrounding the capsule, which produce oscillations of the tubular body 12 at the rhythm of the heartbeats; and/or the various vibrations transmitted by the cardiac tissues.

The pendular unit may in particular be consisted by a piezoelectric beam 24 clamped, at the position 28, at one of its ends, and whose opposite, free end is coupled to a mobile inertial mass 26. The piezoelectric beam 24 is an elastically deformable flexible beam that constitutes, with the inertial mass 26, a pendular system of the mass-spring type. Due to its inertia, the mass 26 subjects the beam 24 to a deformation of the vibratory type on either side of a neutral or non-deformed position corresponding to a stable rest position in the absence of any stress.

Actually, as for its mechanical behaviour, this unit may be equated to a structure of the "clamped/free beam" type, having a natural frequency of oscillation, which is herein the frequency at which the mass-spring system oscillates. It will be noted that this natural frequency of oscillation, typically of the order of a few tens of hertz, is noticeably higher than the frequency of the external cyclic stresses that correspond to the frequency of the heartbeats (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

The beam 24 further performs, by piezoelectric effect, a function of mechanical-electrical transducer making it possible to convert into electrical charges the mechanical bending stress that is applied to it. These charges are collected by electrodes at the surface of the beam to produce an electrical signal that, after rectification, stabilization and filtering, will power the various electronic circuits of the capsule.

The beam is advantageously a beam of the bimorphous type, i.e. capable of generating energy on its two faces when subjected to a deformation. Theses transduction properties are typical of a piezoelectric material, such as the PZT ceramics or the mono-crystals of the PMN-PT, barium titanate or lithium niobate type.

The invention more particularly relates to the arrangement of the clamping 28 that, as exposed in introduction, is one of the critical aspects of the making of an efficient, reliable and easily industrialisable PEH.

Figure 3:
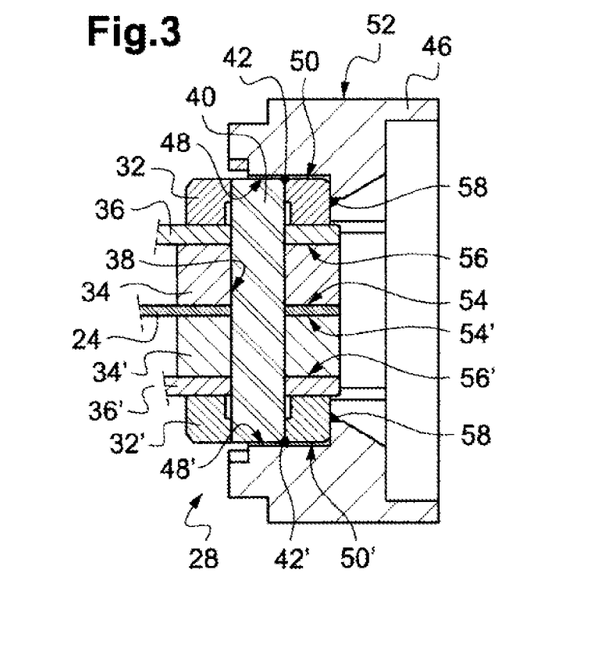
FIG. 3 is a sectional view of the rear portion of the PEH, along the sectional plane A-A of FIG. 2.
Figure 4:
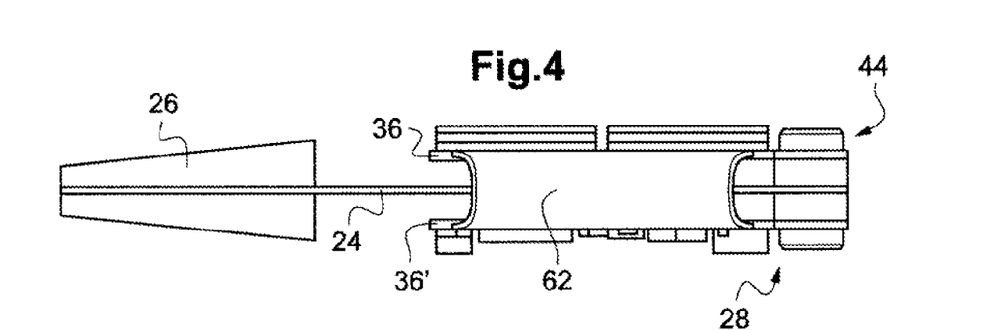
FIG. 4 is an elevation view of the full block integrating the PEH and the PCBs mounted in this block in the same time as the PEH.

FIG. 3 and FIG. 4 illustrate, in perspective and cross-section, the structure of a clamping 28 made according to the teachings of the invention. The different parts illustrated in these figures are also visible in isolation in the exploded perspective of FIG. 8.

The end of the beam 24 located at the opposite of the mobile mass 26 is taken in sandwich at the clamping 28 between two pressing elements 30, 30', preferably symmetrical to each other, between which it is mechanically gripped with a pressure uniformly distributed and controlled by the tightening means that will be described hereinafter. The pressing elements 30, 30' also ensure, on the electrical point of view, a contact with the surface electrodes carried by the beam 24 on either of its two faces, and which allow collecting the electrical charges generated by piezoelectric effect under the effect of the deformations of the beam in its oscillating movement.

Each of the pressing elements 30, 30' includes a respective pressure plate 32, 32' and a respective intermediate part 34, 34' interposed between the pressure plate 32, 32' and the external face of the beam 24 located opposite thereto.

In an advantageous embodiment, a printed circuit board (hereinafter PCB) 36 and/or 36' is also interposed between the respective pressure plate 32, 32' and the intermediate part 34, 34'.

Figure 8:
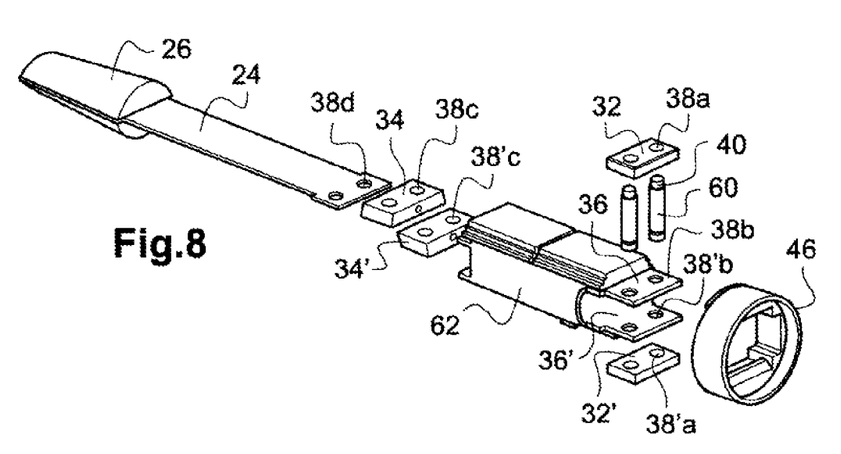
FIG. 8 is an exploded perspective view showing the different constitutive elements of the block of FIG. 4.

In the configuration illustrated in the figures, in which a beam 24 and two PCBs 36, 36' are held together by the pressing elements, it is obtained, at the clamping 28, a stack 44 including successively:
a first pressure plate 32,
a first PCB 36,
a first intermediate part 34,
the piezoelectric beam 24,
a second intermediate part 34',
a second PCB 36', and
a second pressure plate 32'.

The intermediate parts 34, 34' are advantageously made of an electrically conductive material, in particular a metal such as stainless steel, which allows establishing a direct electrical connection between a surface electrode of a first face 54 of the beam 24 and a corresponding conductive plot 56 of the PCB 36, and/or between a surface electrode of a second, opposite face 54' of the beam and a corresponding conductive plot 56' of the PCB 36'. It will be noted that the metal/electrode contact is advantageously made over the whole surface of the beam electrode, hence with an extremely reduced contact impedance.

The stack 44 is moreover passed through by at least one common bore 38 (two bores, in the illustrated example), which is consisted by a series of aligned holes 38a, 38b, 38c, 38d, 38'a, 38'b and 38'a respectively formed in the above-described elements 32, 36, 34, 24, 34', 36' and 32'.

In each of the bores 38 is introduced a pin 40, in the illustrated example a cylindrical metal pin whose length is equal to the total thickness of the stack 44 consisted of the just-described different parts.

To each of its two ends, each pin 40 is fastened to the corresponding pressure plate 32, 32', advantageously by one or several laser welding points, such as 42, 42' (FIG. 3), the pressure plate being for that purpose made of a metallic material such as stainless steel.

The welding of the pins 40 to the pressure plates 32, 32' has for effect to definitively fasten the different parts of the stack 44 to each other and to maintain the assembly under a constant pressure, which is that which was exerted by the pressure plates 32, 32' at the time of the welding operation.

Another advantage, on the electrical point of view, is that a direct connection is obtained between the pressure plates 32, 32', and hence between the external faces of the respective PCBs 36, 36' against which presses the internal faces of these pressure plates, hence offering an additional electrical connection between the two PCBs, for example a ground link.

To avoid any galvanic connection or leak current with the internal faces of the PCBs 36, 36' and/or with the electrodes of the beam 24, the pins 40 are coated over their whole length, except their ends, with an insulator 60 (FIG. 8) such as a heat-shrinkable sleeve or a coating with an insulating material such as parylene, applied under vacuum. As a variant, a functional clearance may be provided between the pin 40 and the internal surface of the bore 38 to avoid these electrical hazards.

Finally, from the mechanical point of view, it will be noted that the presence of one or several holes in the centre of each of the parts passed through by the bore 38 ensures a more uniform distribution of the stresses than with a part that would be devoid of any discontinuity.

The stack 44 and the welded pins 40 form with the PCBs 36, 36' (connected to each other by a layer of flexible conductors 62) a single-piece sub-unit, that is illustrated in side view in FIG. 4.

This sub-unit is mounted in a receptacle of a support part 46 of conjugated shape, with internal faces 48, 48' receiving with no clearance the respective external faces 50, 50' of the pressure plates 32, 32' so as to receive and accurately centre the stack into the support part 46.

The support part 46 is advantageously made of a metal such as titanium, which makes it possible to definitively fasten the stack 44 for example by laser welding points, such as 58 (FIG. 3).

The external face 52 of the support part 50 has for its part a generally cylindrical surface liable to be housed inside the tubular body 12 of the leadless capsule 10 at the time of assembly of the latter.

Figure 2:
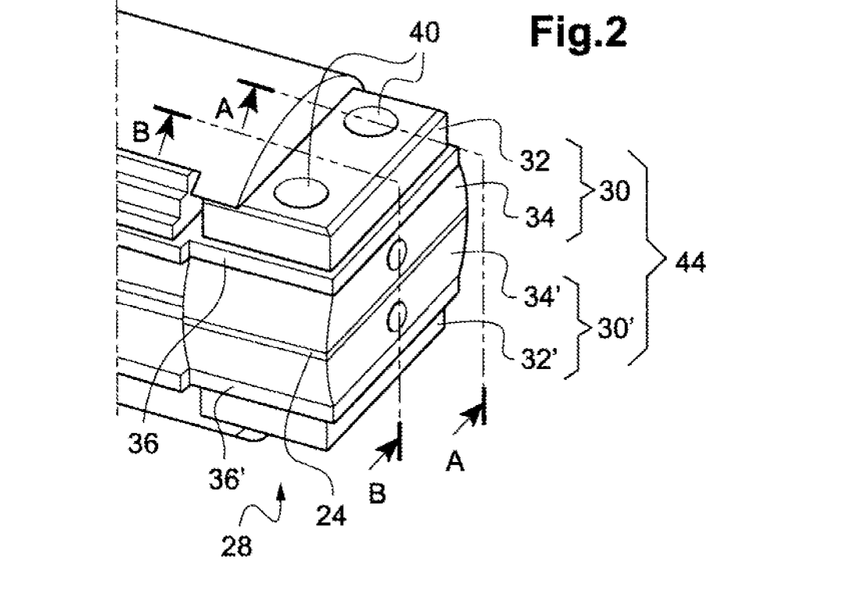
FIG. 2 is a perspective view of the rear portion of the PEH, showing the arrangement of the different elements for the controlled clamping of the beam.
Figure 5:
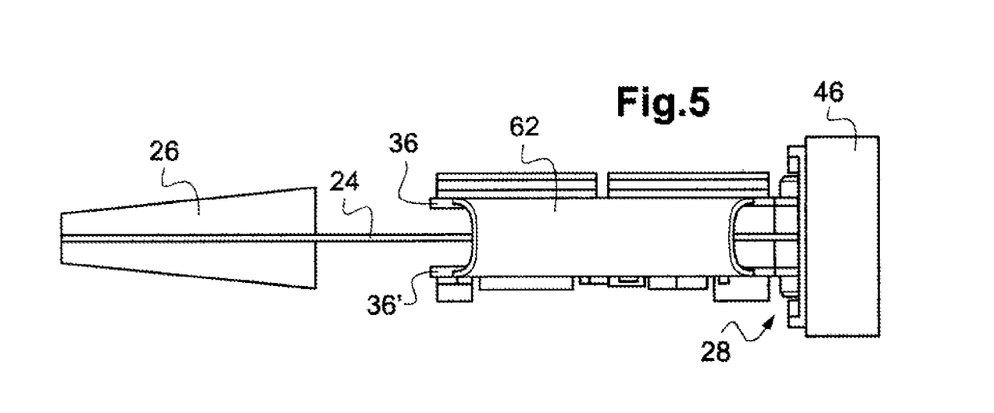
FIG. 5 is similar to FIG. 4, after a support part has been added at the rear of the block for centring and mounting the unit into the tubular body of the implant.
Figure 6:
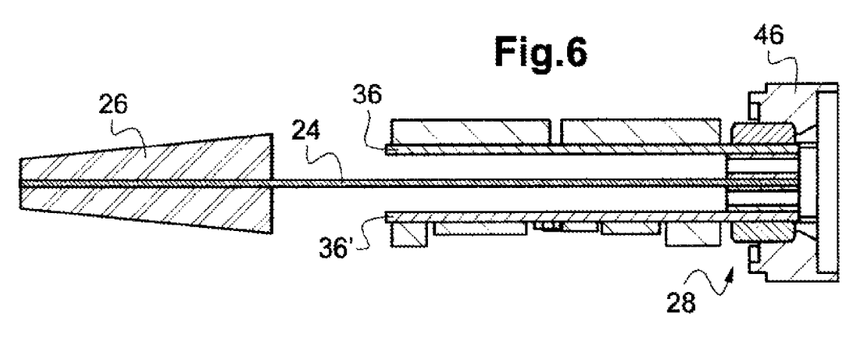
FIG. 6 is a sectional view of the block of FIG. 5, taken along the sectional plane B-B of FIG. 2.
Figure 7:
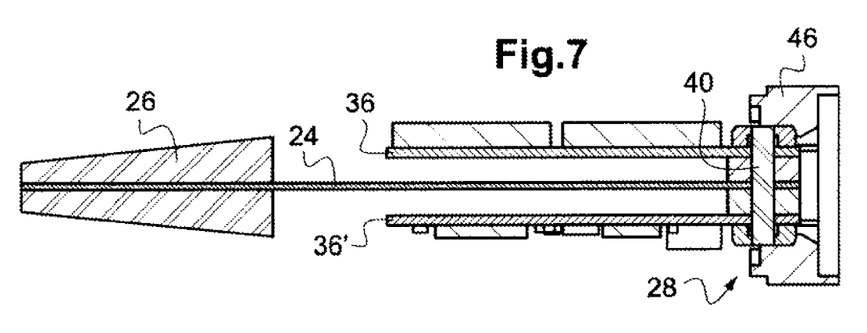
FIG. 7 is a sectional view of the block of FIG. 5, taken along the sectional plane A-A of FIG. 2.
Figure 9:
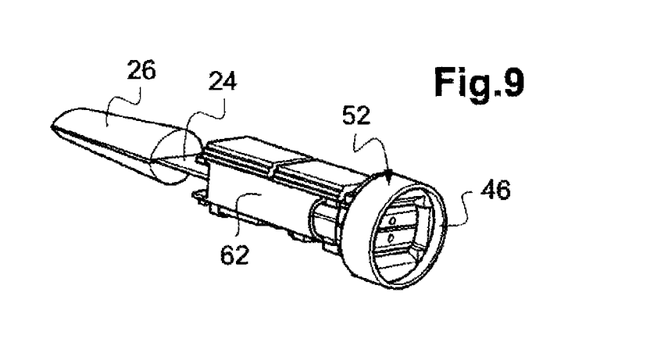
FIG. 9 is similar to FIG. 8, after assembly of the different elements, in a configuration similar to that of FIGS. 5 to 7.

The so-obtained final unit is illustrated: in side view in FIG. 5; in cross-sectional views in FIGS. 6 and 7 (respectively along the sectional planes A-A and B-B of FIG. 2); in exploded perspective view of FIG. 8; and in non-exploded perspective view in FIG. 9.

Figure 10:
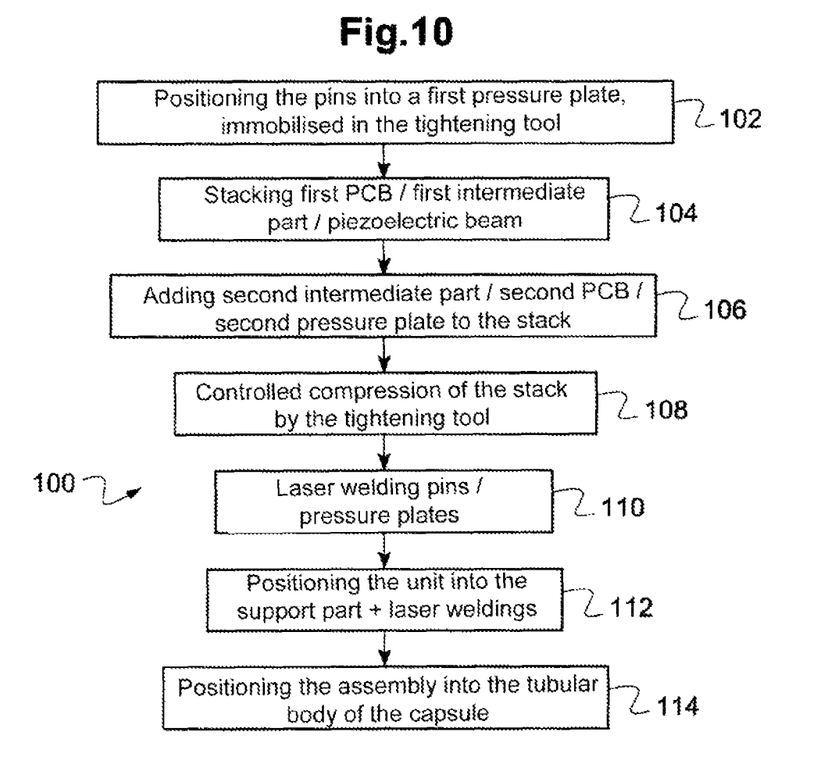
FIG. 10 is a flow-diagram explaining the different steps of the method of making the PEH block according to the invention.

The different successive operations of the assembly process for making the just-described unit will now be described with reference to the flow-diagram 100 of FIG. 10.

The first step (step 102) consists in positioning the two pins 40 into one of the pressure plates, for example the pressure plate 32', itself immobilized in a tightening tool.

The stack 44 is then formed (step 104) by successive addition of: the first PCB 36; the first intermediate part 34'; and the piezoelectric beam 24.

The positioning is continued (step 106) by reiteration of the preceding operations, with addition of the last elements of the stack: the second intermediate part 34; the second PCB 36; finally the second pressure plate 32.

Then, the tightening tool applies (step 108) to the two pressure plates 32, 32', an accurately controlled pressure, typically included between 0.1 MPa and 10 MPa, according to the specific characteristics proper to the piezoelectric beam used.

Laser weldings 42, 42' are then made (step 110) between the pins 40 and each of the pressure plates 32, 32'.

Once this sub-system assembled (corresponding to that illustrated in FIG. 4), it is positioned (step 112) in the support and centring part 46, to which it is fastened by laser weldings 58 made between the pressure plates 32, 32' and the support part 46. The so-obtained assembly is that illustrated in FIGS. 5 and 9.

This assembly is finally placed into the tubular body 12 of the leadless capsule (step 114) by positioning, centring and fastening per se known techniques, as those described for example in US 2019/381325 A1 (Regnier).

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

1. An active medical device of an autonomous implantable capsule type, comprising an elongated tubular envelope housing an energy harvesting module, wherein
   the energy harvesting module comprises an oscillating pendular unit subjected to external stresses applied to the tubular envelope,
   the oscillating pendular unit comprising an elastically deformable piezoelectric beam having a clamped end and an opposite, free end coupled to an inertial mass,
   the piezoelectric beam being adapted to convert into an oscillating electric signal a mechanical energy produced by oscillations of the pendular unit, wherein
   the tubular envelope also houses a beam frame,
   the beam frame comprising two pressing elements sandwiching the clamped end of the piezoelectric beam, and means for tightening the pressing elements together, wherein
   each pressing element of the beam frame comprises:
   i) an intermediate part, an internal face of which presses on a corresponding face of the piezoelectric beam, and
   ii) a pressure plate, an internal face of which presses on an external face of the intermediate part,
   wherein the intermediate parts and the pressure plates of the two pressing elements are passed through by at least one common bore extending in a transverse direction with respect to a longitudinal axis of the piezoelectric beam,
   said at least one common bore receiving a locking pin, and wherein the beam frame further comprises means for holding and fastening the pin in position in said at least one common bore.

2. The device of claim 1, wherein the means for holding and fastening the pin in position comprises laser welding of a free end of the pin at an open edge of the common bore.

3. The device of claim 1, wherein the intermediate part, an internal face of which presses against a corresponding face of the piezoelectric beam, is in mechanical contact with said corresponding face of the piezoelectric beam.

4. The device of claim 3, wherein the intermediate part comprises on the internal face thereof a conductive material capable of further establishing an electrical contact with said corresponding face of the piezoelectric beam, at a surface electrode of said piezoelectric beam.

5. The device of claim 1, further comprising a printed circuit board interposed between the intermediate part and the pressure plate of at least one of the pressing elements of the beam frame, and wherein the pressure plate comprises, on an internal face, a conductive material in electrical contact with the corresponding external face of the printed circuit board.

6. The device of claim 5, wherein the intermediate part comprises, on its internal face, a conductive material capable of establishing an electrical contact with said corresponding face of the piezoelectric beam, at a surface electrode of said piezoelectric beam, the intermediate part comprises, on its external face, a conductive material capable of establishing an electrical contact with an internal face of the printed circuit board, and the conductive materials of the internal and external faces of the intermediate part are electrically coupled to each other.

7. The device of claim 6, wherein the intermediate part is a single-piece part formed of a single conductive material.

8. The device of claim 1, wherein the intermediate parts, the pressure plates and the pin are each massive metal parts.

9. The device of claim 1, wherein the beam frame is essentially devoid of an element interposed between the intermediate parts and the clamped end of the piezoelectric beam.

10. The device of claim 1, wherein the beam frame is essentially devoid of bonding points.

11. The device of claim 1, wherein the elongated tubular envelope also houses a support part having an external tubular shape mating an internal shape of the tubular envelope, and comprising at one of its ends a receptacle capable of receiving and centring the beam frame and of fastening the latter by press-fit at external faces of the pressure plates.

12. The device of claim 1, wherein the pin is a metal part coated with an electrically insulating material adapted to avoid a galvanic connection and/or a leak current within the piezoelectric beam.

13. A method of manufacturing a device according to claim 1, comprising the following steps:
   a) obtaining a piezoelectric beam;
   b) placing a pressing element on each side of a clamped end of the piezoelectric beam, each pressing element comprising i) an intermediate part, an internal face of which presses on a corresponding face of the piezoelectric beam, and ii) a pressure plate, an internal face of which presses on an external face of the intermediate part, optionally with a printed circuit board interposed between the intermediate part and the pressure plate of at least one of the pressing elements of the beam frame;
   c) positioning a pin into a common bore passing through the intermediate parts and the pressure plates of the two pressing elements in a transverse direction with respect to a longitudinal axis of the piezoelectric beam;
   d) pressing the beam under controlled pressure between the two pressing elements, until reaching a predetermined transverse force of clamping of the piezoelectric beam between the two pressing elements; and
   e) while maintaining said predetermined transverse force, definitively fastening the pin into said at least one common bore.

14. The method of claim 13, wherein step e) is a step of laser welding of a free end of the pin to an open edge of the common bore.

15. The method of claim 13, wherein the method is essentially devoid of a bonding step.

16. The method of claim 13, wherein said controlled pressure exerted on the beam between the two pressing elements is between 0.1 MPa and 10 MPa.

* * * * *